United States Patent
Gellman et al.

(10) Patent No.: US 8,562,646 B2
(45) Date of Patent: Oct. 22, 2013

(54) ANCHORING TO SOFT TISSUE

(75) Inventors: Barry N. Gellman, N. Easton, MA (US); Armond A. Morin, Berkeley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2044 days.

(21) Appl. No.: 10/325,125

(22) Filed: Dec. 19, 2002

(65) Prior Publication Data
US 2004/0122474 A1  Jun. 24, 2004

(51) Int. Cl.
*A61B 17/04* (2006.01)
*A61F 2/02* (2006.01)

(52) U.S. Cl.
USPC .............................. 606/232; 600/30

(58) Field of Classification Search
USPC ............... 606/72–75, 86, 232, 213, 215, 216, 606/217, 218, 225, 219; 623/13.13, 13.14; 411/55; 600/29, 37
See application file for complete search history.

(56) References Cited

U.S. PATENT DOCUMENTS

| | | | |
|---|---|---|---|
| 2,143,910 A * | 1/1939 | Didusch | 606/151 |
| 4,006,747 A | 2/1977 | Kronenthal et al. | |
| 4,172,458 A | 10/1979 | Pereyra | |
| 4,669,473 A | 6/1987 | Richards et al. | |
| 4,705,040 A | 11/1987 | Mueller et al. | |
| 4,938,760 A | 7/1990 | Burton et al. | |
| 5,013,292 A | 5/1991 | Lemay | |
| 5,041,129 A | 8/1991 | Hayhurst et al. | |
| 5,085,661 A | 2/1992 | Moss | |
| 5,149,329 A | 9/1992 | Richardson | |
| 5,207,679 A | 5/1993 | Li | |
| 5,256,133 A | 10/1993 | Spitz | |
| 5,312,438 A | 5/1994 | Johnson | |
| 5,370,661 A | 12/1994 | Branch | |
| 5,462,561 A * | 10/1995 | Voda | 606/144 |
| 5,501,695 A * | 3/1996 | Anspach et al. | 606/232 |
| 5,549,617 A | 8/1996 | Green et al. | |
| 5,562,689 A | 10/1996 | Green et al. | |
| 5,611,515 A | 3/1997 | Benderev et al. | |
| 5,643,288 A | 7/1997 | Thompson | |
| 5,645,589 A | 7/1997 | Li | |
| 5,647,836 A | 7/1997 | Blake et al. | |
| 5,674,247 A | 10/1997 | Sohn | |
| 5,697,931 A | 12/1997 | Thompson | |
| 5,702,215 A | 12/1997 | Li | |
| 5,702,421 A | 12/1997 | Schneidt | |
| 5,816,258 A | 10/1998 | Jervis | |
| 5,954,057 A | 9/1999 | Li | |
| 5,997,556 A | 12/1999 | Tanner | |
| 6,030,393 A | 2/2000 | Corlew | |
| 6,039,686 A | 3/2000 | Kovac | |
| 6,042,534 A | 3/2000 | Gellman et al. | |

(Continued)

FOREIGN PATENT DOCUMENTS

| WO | WO 96/40356 | 12/1996 |
|---|---|---|
| WO | WO 01/21247 | 3/2001 |
| WO | WO 01/97676 A2 | 12/2001 |
| WO | WO 02/17771 A2 | 3/2002 |

*Primary Examiner* — Tuan V Nguyen

(57) ABSTRACT

Soft tissue anchors can be used in various surgical procedures, including pelvic floor reconstruction procedures. The anchors have one position that allows passage through the body and another position that inhibits passage of the anchors back through the soft tissue when a pull-back force is applied to the anchors by an implant, such as a surgical sling used for support of the urethra.

13 Claims, 15 Drawing Sheets

(56) References Cited

U.S. PATENT DOCUMENTS

| | | |
|---|---|---|
| 6,056,760 A | 5/2000 | Koike et al. |
| 6,059,801 A | 5/2000 | Samimi |
| 6,113,611 A | 9/2000 | Allen et al. |
| 6,231,561 B1 * | 5/2001 | Frazier et al. ................. 604/500 |
| 6,245,082 B1 | 6/2001 | Gellman et al. |
| 6,273,852 B1 | 8/2001 | Lehe et al. |
| 6,306,079 B1 | 10/2001 | Trabucco |
| 6,319,272 B1 | 11/2001 | Brenneman et al. |
| 6,322,492 B1 | 11/2001 | Kovac |
| 6,328,686 B1 | 12/2001 | Kovac |
| 6,328,758 B1 * | 12/2001 | Tornier et al. ................. 606/232 |
| 6,382,214 B1 | 5/2002 | Raz et al. |
| 6,387,041 B1 | 5/2002 | Harari et al. |
| 6,406,234 B2 | 6/2002 | Frigg |
| 6,406,423 B1 | 6/2002 | Scetbon |
| 6,423,080 B1 | 7/2002 | Gellman et al. |
| 6,428,562 B2 | 8/2002 | Bonutti |
| 6,447,524 B1 | 9/2002 | Knodel et al. |
| 6,482,210 B1 | 11/2002 | Skiba et al. |
| 6,537,198 B1 | 3/2003 | Vidlund et al. |
| 6,960,160 B2 * | 11/2005 | Browning ................. 600/37 |
| 2001/0039423 A1 | 11/2001 | Skiba et al. |
| 2002/0161382 A1 | 10/2002 | Neisz et al. |
| 2002/0183786 A1 | 12/2002 | Girton |
| 2003/0045893 A1 | 3/2003 | Ginn |
| 2003/0050665 A1 | 3/2003 | Ginn |

* cited by examiner

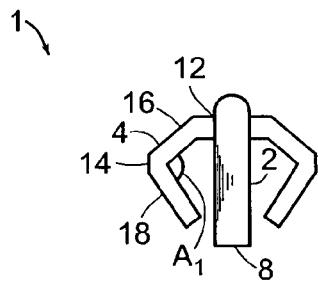
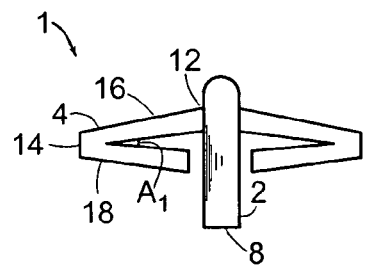
FIG. 8　　　　　FIG. 9
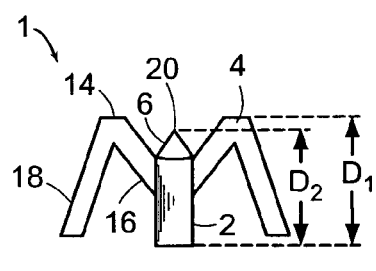
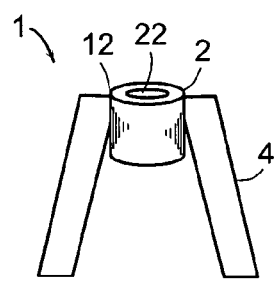
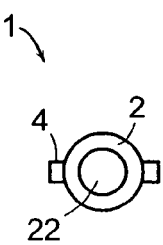
FIG. 10　　　FIG. 11A　　　FIG. 11B
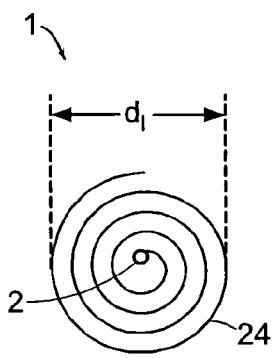
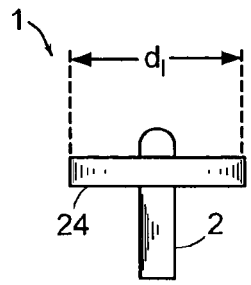
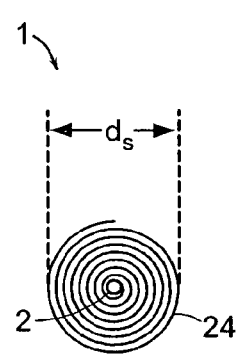
FIG. 12A　　　FIG. 12B　　　FIG. 13

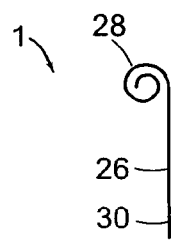
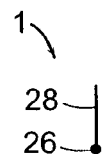
FIG. 14A  FIG. 14B
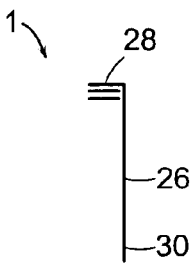
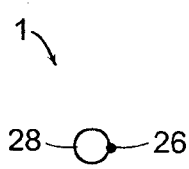
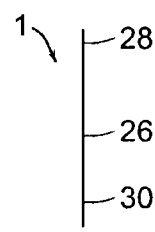
FIG. 15A  FIG. 15B  FIG. 16
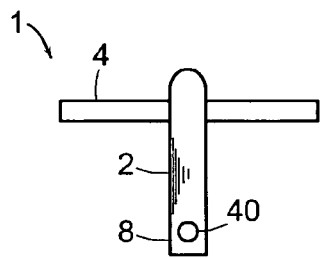
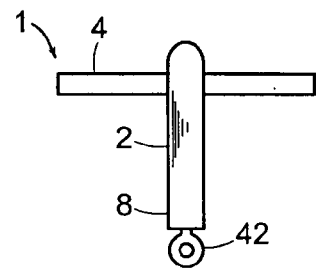
FIG. 17  FIG. 18
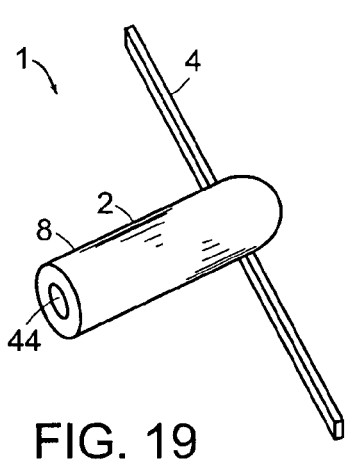
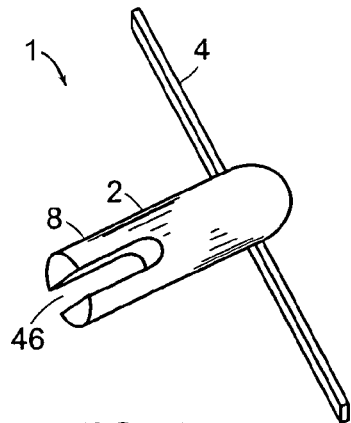
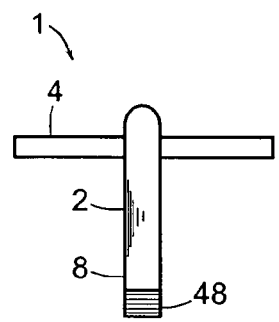
FIG. 19  FIG. 20  FIG. 21

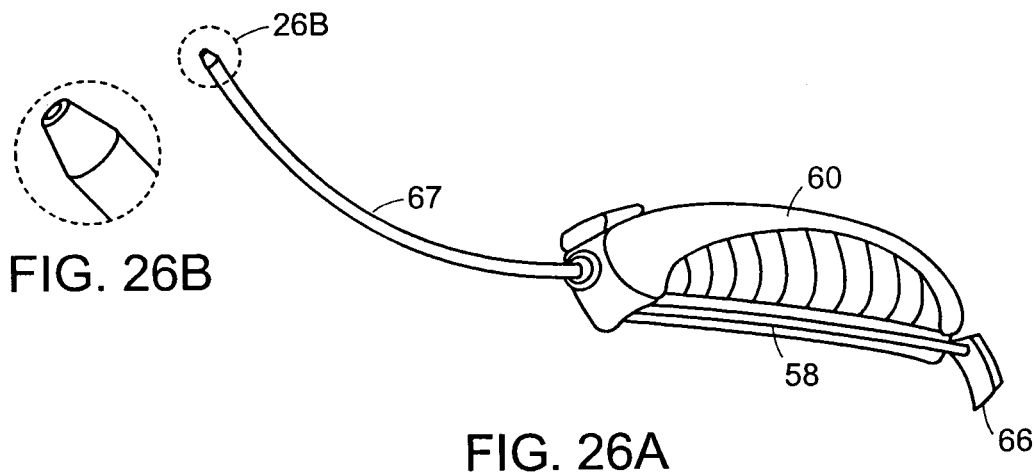
FIG. 26B
FIG. 26A
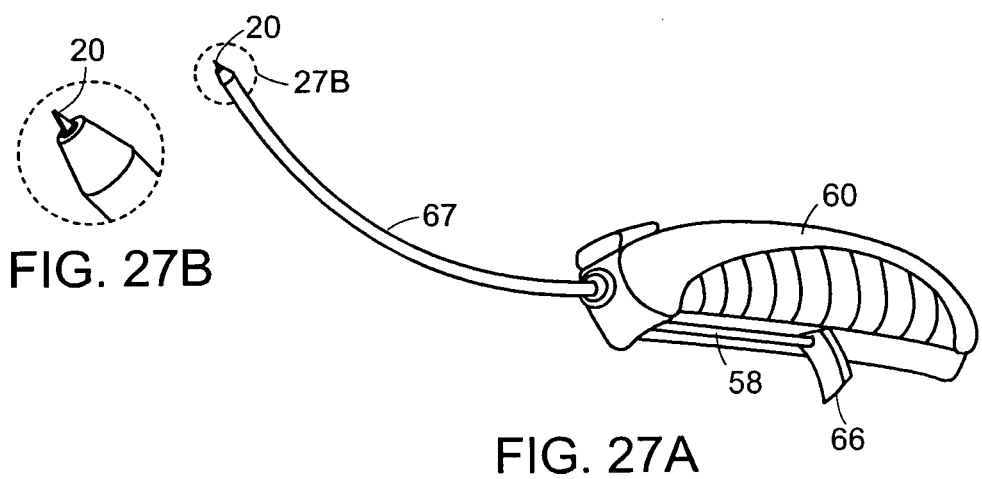
FIG. 27B
FIG. 27A
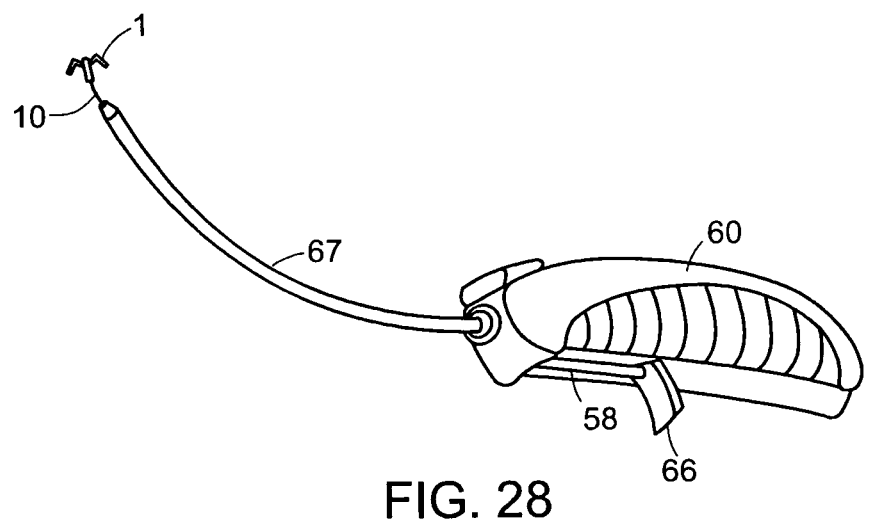
FIG. 28

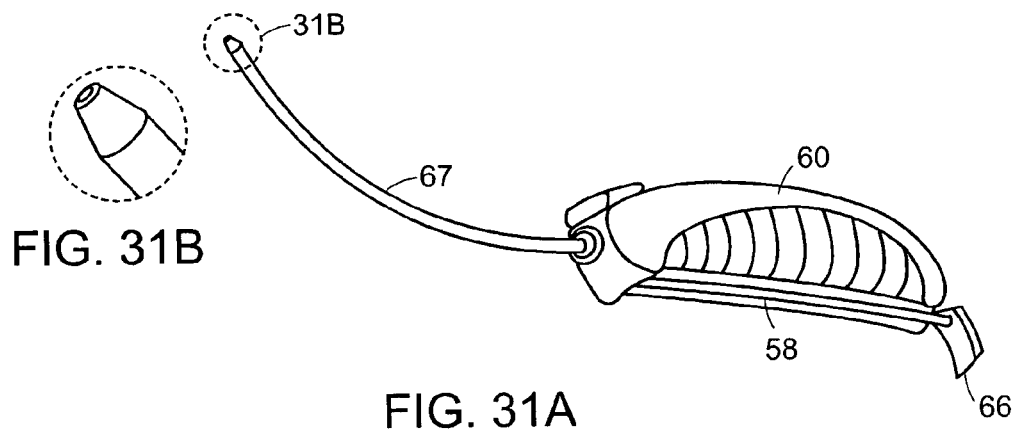
FIG. 31B
FIG. 31A
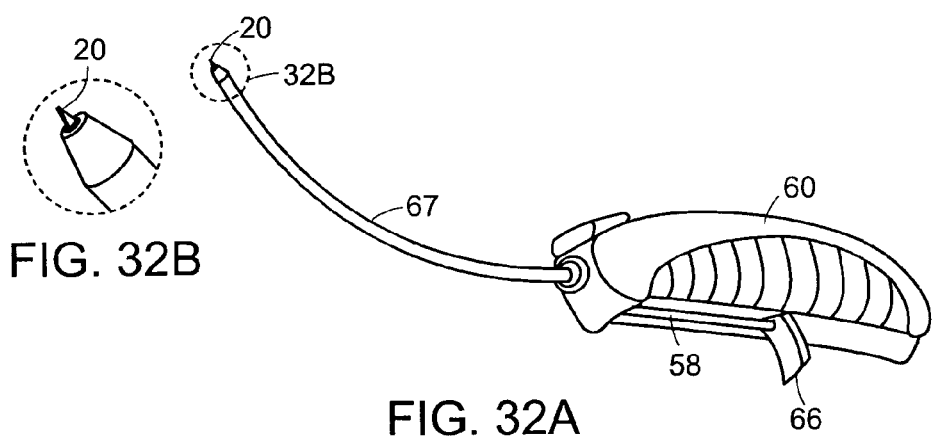
FIG. 32B
FIG. 32A
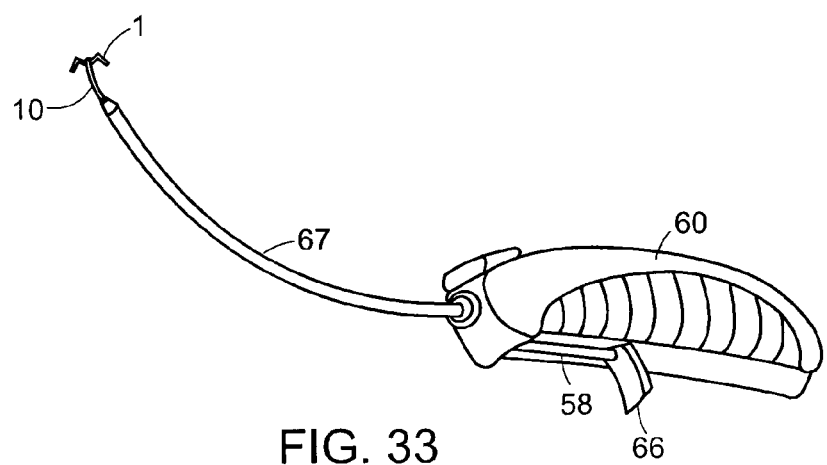
FIG. 33

ANCHORING TO SOFT TISSUE

TECHNICAL FIELD

This invention generally relates to anchoring an implant within the body of a patient. More particularly, the invention relates to devices that anchor implants to soft tissue for use in surgical procedures, for example, pelvic floor reconstruction procedures.

BACKGROUND INFORMATION

Certain urinary and gynecological pathologies can be treated by stabilizing an organ or tissue within the pelvic region. In female patients, examples of pathologies that can be treated by such a procedure include vaginal, uterine, and rectal prolapses, cystoceles, lateral defects, and urinary incontinence. A known method for stabilizing organs and tissues within the pelvic region involves the use of bone anchors. Deployment of a bone anchor requires drilling a hole in a bone, either by using a separate drilling instrument or by utilizing the anchor itself as a drilling tool. Bone anchors generally have one or more barbs that project outward to prevent the anchor from exiting the hole. Such anchors generally are not amenable to implantation in soft tissues, since the barbs would tear the soft tissue, causing irritation and/or passage of the anchor back through the tissue.

Other known methods include making one or more incisions in a patient's abdomen. For example, one method for treating female stress urinary incontinence involves supporting the urethra with an implant anchored in the patient's skin after the implant has been passed through the skin of the patient's abdomen.

SUMMARY OF THE INVENTION

The present invention relates to devices that anchor implants to soft tissue for use in surgical procedures, for example, pelvic floor reconstruction procedures. The devices, or soft tissue anchors, and the delivery systems for the anchors generally are for use by surgeons and/or other medical professionals. Anchors according to the invention can be used to treat, for example, female stress urinary incontinence (SUI) by using an appropriate delivery system to deliver one or more anchors and a corresponding implant (such as a urethral sling) transvaginally, thus avoiding altogether the need for abdominal incisions. The structural tear resistance of the abdominal muscle is used to provide a stable and durable anchoring point in such transvaginal procedures. This results in a simpler and faster procedure than other therapies that involve making abdominal incisions and/or drilling into the pubic bone to place anchors. Although soft tissue anchors according to the invention preferably are used in transvaginal procedures, the anchors also can be used in other procedures that do require abdominal incisions. Soft tissue anchors according to the invention have one or more support members or arms that rest upon the surface of the soft tissue and provide pull-through support without irritating tissue. The anchors can be used in a variety of surgical procedures and can support a variety of implants, including a surgical mesh or a surgical sling. In general, a soft tissue anchor according to the invention has one position that allows passage through the soft tissue of a patient and another position that inhibits passage of the anchor through the penetrated soft tissue when a pull-back force is applied to the anchor by an implant, such as a urethral sling, that is coupled to the anchor.

In general, in one aspect, the invention features a soft tissue anchor that comprises a central body element and a plurality of support members radially disposed about the central body element. The central body element comprises a proximal portion that can receive an implant. Each of the support members can move between a first position, which permits passage of the anchor through the soft tissue, and a second position, which inhibits passage of the soft tissue anchor back through the soft tissue when a pull-back force is applied to the anchor by the implant.

Embodiments of this aspect of the invention can include the following features. Each of the support members can be cantilevered, with the first position being laterally inward proximate to the central body element and the second position being laterally outward from the central body element. Each of the support members can be biased in the second position. The support members can also be collapsible and expandable structures, with the second position being the collapsed position. The distal portion of the central body element can taper to a point for penetrating soft tissue. A soft tissue anchor with a pointed distal end can include support members that prevent the point from contacting soft tissue when in the second position. Alternatively, the central body element can define an aperture and a passageway through its center. The proximal portion of the central body element can include an aperture, an eyelet, a groove, or a lumen for receiving an implant. Alternatively, at least some of the proximal portion can include threads for receiving a mating member, which can be coupled to an implant. The implant itself can include a surgical mesh, a surgical sling, or one or more sutures. The soft tissue anchor can be fabricated from at least one bio-compatible material, such as a metal or a polymer.

In general, in another aspect, the invention features a central body element comprising a proximal portion for receiving an implant and one or more support members disposed about the central body element. Each of the support members can move between a first position, wherein the support member is wrapped around the central body element to permit passage of the soft tissue anchor through the soft tissue, and a second position, wherein each of the support members is projected outward from the central body element to inhibit passage of the soft tissue anchor back through the soft tissue when a force is applied to the anchor by the implant.

Embodiments of this aspect of the invention can include the following features. Each of the one or more supports can be biased in the second position. The proximal portion of the central body element can include an aperture, an eyelet, a groove, a lumen, or threads, and the implant can include a surgical mesh, a surgical sling, or suture(s). The soft tissue anchor can be fabricated from at least one bio-compatible material, such as a metal or a polymer.

In general, in yet another aspect, the invention features a soft tissue anchor comprising a distal portion comprising one or more coils that, when acted upon by a restraining force, adopt a shape that permits passage of the anchor through soft tissue. Upon removal of the restraining force, the one or more coils return to the coiled shape which inhibits passage of the soft tissue anchor back through the soft tissue when a force is applied to the anchor. The soft tissue anchor also comprises a proximal portion that extends from the distal portion and receives an implant.

Embodiments of this aspect of the invention can include the following features. The coiled distal portion can lie substantially in the same plane as the longitudinal axis of the proximal portion, or it can lie in a different plane than the longitudinal axis of the proximal portion. The proximal portion of the central body element can include an aperture, an eyelet, a groove, a lumen, or threads, and the implant can include a surgical mesh, a surgical sling, or suture(s). The soft tissue anchor can be fabricated from at least one bio-compatible material, such as a metal or a polymer.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 8 is a side view of another embodiment of a soft tissue anchor, in an expanded first position.

FIG. 9 is a side view of the soft tissue anchor of FIG. 8, but in a collapsed second position.

FIG. 10 is a side view of another embodiment of a soft tissue anchor with a distal portion that tapers to a point, with the distances $D_1$ and $D_2$ indicated.

FIG. 11a is a side view of another embodiment of a soft tissue anchor, with a central body element that defines an aperture with a passageway through its center.

FIG. 11b is a top view of the soft tissue anchor of FIG. 1a.

FIG. 12a is a top view of another embodiment of a soft tissue anchor, with a support member that forms a coil around the central body element, in a second position.

FIG. 12b is a side view of the soft tissue anchor of FIG. 12a.

FIG. 13 is a top view of the soft tissue anchor of FIG. 12a, but in a first position.

FIG. 14a is a side view of another embodiment of a soft tissue anchor in a second position, and this anchor comprises an element with a coiled distal end that lies substantially in the same plane as the longitudinal axis of the element's proximal end.

FIG. 14b is a top view of the soft tissue anchor of FIG. 14a.

FIG. 15a is a side view of another embodiment of a soft tissue anchor in a second position, and this anchor comprises an element with a coiled distal end that does not lie in the same plane as the longitudinal axis of the element's proximal end.

FIG. 15b is a top view of the soft tissue anchor of FIG. 15a.

FIG. 16 is a side view of the soft tissue anchor of FIG. 14 or FIG. 15a, in a first position.

FIG. 17 is a side view of another embodiment of a soft tissue anchor, with a proximal portion that includes an aperture for receiving an implant.

FIG. 18 is a side view of another embodiment of a soft tissue anchor, with a proximal portion that includes an eyelet for receiving an implant.

FIG. 19 is a side view of another embodiment of a soft tissue anchor, with a proximal portion that defines a lumen for receiving an implant.

FIG. 20 is a side view of another embodiment of a soft tissue anchor, with a proximal portion that defines a groove for receiving an implant.

FIG. 21 is a side view of another embodiment of a soft tissue anchor, with a proximal portion that includes threads for receiving an implant.

FIG. 22b is a magnified view of the distal end of the delivery device of FIG. 22a.

FIG. 23b is a magnified view of the distal end of an embodiment of the cartridge of FIG. 23a.

FIG. 26a is a side perspective view of the delivery device of FIG. 25, with the cartridge of FIG. 23a inserted and in position A.

FIG. 26b is a magnified view of the distal end of the delivery device of FIG. 26a.

FIG. 27a is a view corresponding to FIG. 26a, with the cartridge in position B.

FIG. 27b is a magnified view of the distal end of the delivery device of FIG. 27a.

FIG. 28 is a view corresponding to FIG. 26a, with the cartridge in position C.

FIG. 31a is a side perspective view of the delivery device of FIG. 25, with the cartridge of FIG. 29 inserted and in position A.

FIG. 31b is a magnified view of the distal end of the delivery device of FIG. 31a.

FIG. 32a is a view corresponding to FIG. 31a, with the cartridge in position B.

FIG. 32b is a magnified view of the distal end of the delivery device of FIG. 32a.

FIG. 33 is a view corresponding to FIG. 31a, with the cartridge in position C.

DESCRIPTION

Figure 1:
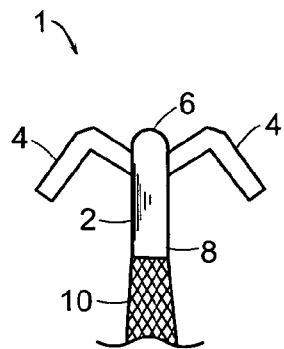
FIG. 1 is a side view of an embodiment of a soft tissue anchor coupled to an implant, according to the present invention.

In general, the invention relates to a soft tissue anchor for supporting an implant within the body of a patient. Referring to FIG. 1, in one disclosed embodiment according to the invention, the soft tissue anchor 1 includes a central body element 2 from which a plurality of support members 4 project. The central body element 2 includes a distal portion 6 and a proximal portion 8. The proximal portion 8 includes a structure, such as an aperture or an eyelet, to which an implant 10, such as a surgical mesh or sling, may be coupled. Ways of coupling the implant 10 to the proximal portion 8 include tying, threading, crimping, affixing with an adhesive, or the like. Other ways of coupling the implant 10 to the proximal portion 8 are also possible.

Figure 2:
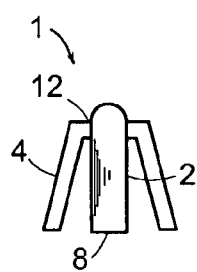
FIG. 2 is a side view of another embodiment of a soft tissue anchor, in a first position.
Figure 3:
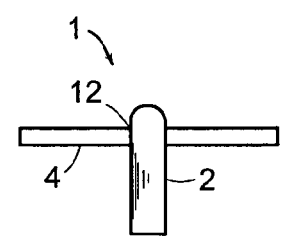
FIG. 3 is a side view of the soft tissue anchor of FIG. 2, but in a second position.

Referring to FIG. 2 each support member 4 is a cantilevered support projecting from the central body element 2 at point 12. Each support member 4 is capable of pivoting at point 12 between a first position, illustrated by FIG. 2, wherein the support member 4 is articulated inward toward the proximal portion 8 of central body element 2, and a second position, illustrated by FIG. 3, wherein the support member 4 is articulated laterally away from the central body element 2. Each support member 4 can be biased in the second position such that it assumes that laterally extended second position when unrestrained. Alternatively, each support member 4 can be formed of a shape-memory material that assumes the second position upon, for example, a temperature change (from, for example, ambient/room temperature where it is in the first position to body temperature where it is in the second position).

Figure 4:
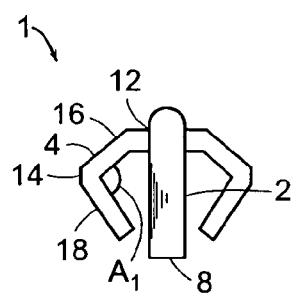
FIG. 4 is a side view of another embodiment of a soft tissue anchor, in a first position.
Figure 5:
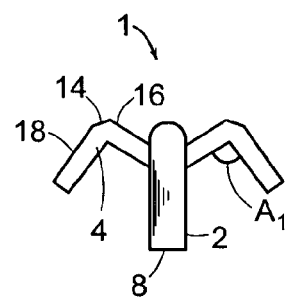
FIG. 5 is a side view of the soft tissue anchor of FIG. 4, but in a second position.
Figure 6:
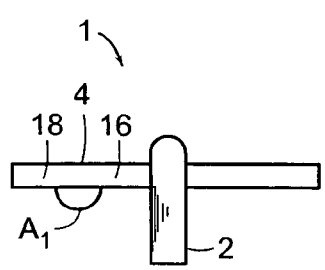
FIG. 6 is also side view of a soft tissue anchor of FIG. 4, but in an alternative second position.

Referring to FIG. 4, in another embodiment, each support member 4 contains an elbow 14 that divides the support member 4 into an upper portion 16 and a lower portion 18. Each support member 4 is bent at the elbow 14 so that the lower portion 18 is deflected inward toward the central body element 2 in the proximal direction, defining an interior angle $A_1$ between the lower portion 18 and the upper portion 16 which is less than 180 degrees. Each support member 4 is capable of pivoting at point 12 between a first position, illustrated by FIG. 4, wherein each support member 4 is articulated inward toward the proximal portion 8 of central body element 2, and a second position, illustrated by FIG. 5, wherein each support member 4 is articulated laterally away from the central body element 2. Each support member 4 can be compliant and resilient and biased in the bent position at the elbow 14, whereby the interior angle $A_1$ is less than 180 degrees. When acted upon by a restraining force, the lower portion 18 of each support member 4 can be articulated such that the interior angle $A_1$ approaches or equals, but generally does not exceed, 180 degrees, as illustrated by FIG. 6. When the restraining force is removed, each support member 4 can return to its bent position at the elbow 14.

Figure 7:
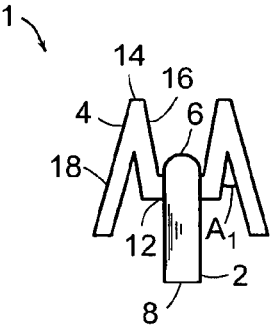
FIG. 7 is a side view of another embodiment of a soft tissue anchor, in a first position.

Referring to FIG. 7, in another embodiment, the soft tissue anchor 1 can adopt a first position wherein each support member 4 is pivoted at the point 12 inward toward the distal portion 6 of central body element 2. At the same time, the lower portion 18 of each support member 4 is bent in a proximal direction at the elbow 14, thereby reducing the interior angle $A_1$ between the upper portion 16 and the lower portion 18.

Referring to FIG. 8, in another embodiment, each support member 4 is bent at a compliant elbow 14 that divides the support member 4 into an upper portion 16 and a lower portion 18. Each support member 4 is bent at the elbow 14 so that the lower portion 18 is deflected inward toward the central body element 2 in the proximal direction, defining an interior angle $A_1$ between the upper portion 16 and the lower portion 18 which is less than 180 degrees. The soft tissue anchor 1 can adopt an expanded first position wherein each support member 4 is pivoted inward at the point 12 toward the lateral portion 8 of central body element 2. At the same time, each support member 4 may also be bent at the elbow 14 such that angle $A_1$ approaches or equals, but generally does not exceed, 180 degrees. Referring to FIG. 9, the soft tissue anchor 1 can adopt a collapsed second position wherein the upper portion 16 of each support member 4 is pivoted laterally away from the central body element 2 at the point 12. At the same time, the elbow 14 is bent such that the angle $A_1$ is reduced, pivoting the lower portion 18 at the elbow 14 to a position closer to the upper portion 16. Each support member 4 can be biased in the collapsed second position, as illustrated by FIG. 9. Alternatively, each support member 4 can be formed of a shape-memory material that assumes the collapsed second position upon, for example, a temperature change (from, for example, ambient/room temperature where it is in the expanded first position to body temperature where it is in the collapsed second position).

Referring to FIG. 10, in one embodiment, the distal portion 6 of the central body element 2 is tapered to a point 20. Each support member 4 can be bent at the elbow 14 so that the lower portion 18 is deflected inward toward the central body element 2 in the proximal direction. As illustrated by FIG. 10, when each support member 4 is in the second position, wherein each support member 4 is articulated laterally away from the central body element 2, the distance $D_1$ from the distal end of the central body element 2 to each elbow 14 is greater than the distance $D_2$ from the distal end of the central body element 2 to the tip of point 20. When the soft tissue anchor 1 according to this embodiment is positioned within the patient, the patient's anterior tissue will contact each elbow 14 rather than the point 20, thus protecting the anterior tissue from abrasion by the point 20.

Referring to FIGS. 11a and 11b, in another embodiment, the central body element 2 is hollow, defining an aperture 22 that runs through the length of central body element 2. The central body element 2 can be cylindrical, defining a round aperture 22. Alternatively, the central body element can be polygonal, defining a polygonal aperture.

Referring to FIGS. 12a and 12b, in another embodiment, the soft tissue anchor 1 contains a single support member 4 forming a coil 24 around a central body element 2. Referring to FIG. 13, when acted upon by a restraining force, the soft tissue anchor 1 can adopt a first position wherein the coil 24 is wrapped tightly around the central body element 2, decreasing the diameter of the coil 24 to a smaller diameter $d_2$. Referring again to FIG. 12a, when the restraining force is removed, the soft tissue anchor 1 can adopt a second position, wherein the coil 24 returns to its more loosely-coiled configuration with a larger diameter $d_1$.

Referring to FIGS. 14a and 14b, in another embodiment, the soft tissue anchor 1 comprises a compliant and resilient element 26 with a coiled distal portion 28 and an uncoiled proximal portion 30. The element 26 can be solid or can comprise a tube with its distal end closed. The coiled distal portion 28 can lie substantially in the same plane as the longitudinal axis of the uncoiled proximal portion 30, as illustrated in FIGS. 14a and 14b. Alternatively, the coiled distal portion 28 can lie in a different plane than the longitudinal axis of the uncoiled proximal portion 30, as illustrated by FIGS. 15a and 15b. Referring to FIG. 16, when acted upon by a restraining force, the coiled distal portion 28 can be deformed into a configuration that is substantially linear with the longitudinal axis of the uncoiled proximal portion 30. This restraining force can be applied manually by the operator in preparation for loading the soft tissue anchor 1 into a delivery device, such as a cannula. When the soft tissue anchor 1 is in the delivery device, the delivery device itself provides the restraining force and maintains the soft tissue anchor 1 in the first position. When the soft tissue anchor 1 is ejected from the delivery device, the restraining force is removed and the distal portion 28 returns to its coiled configuration, illustrated alternatively by FIGS. 14a and 15a.

The proximal portion 8 can include any of a number of structures capable of coupling an implant to the soft tissue anchor 1. The structure can be an aperture 40, as illustrated by FIG. 17, or an eyelet 42, as illustrated by FIG. 18. The structure can also be a lumen 44, as illustrated by FIG. 19, or a groove 46, as illustrated by FIG. 20. Alternatively, referring to FIG. 21, at least some of the proximal portion 8 can contain threads 48 to which a threaded mating element can be coupled, and the mating element can have the implant coupled thereto in any of a variety of ways, such as tying, crimping, or affixing with an adhesive, for example.

A soft tissue anchor 1 described herein can be fabricated from one or more polymers, including polyolefin, polycarbonate, nylon, and/or other bio-compatible thermoplastic or thermoset materials. Alternatively, a soft tissue anchor 1 can be fabricated from one or more metals, including stainless steel, titanium, tantalum, and/or other bio-compatible metals, or it can be fabricated from a metal alloy, such as nickel/titanium or Nitinol.

In one embodiment, the implant 10 is a surgical mesh. The surgical mesh can be fabricated from one or more bio-compatible materials, including polypropylene, polyesters, polyolefins, polytetrafluoroethylene, polyethylene, polyurethanes, nylons, and co-polymers thereof. Alternatively, the surgical mesh can be fabricated from naturally occurring tissue, or a hybrid of synthetic materials and naturally occurring tissues. The surgical mesh may also be made of absorbable materials, such as polyglycolic acid and polylactic acid.

Alternatively, the implant 10 can be a tape or a sling. The tape or sling may be fabricated from any of a variety of synthetic and/or naturally occurring bio-compatible materials. Such materials may be filamentous or non-filamentous, elastic or inelastic, and may be porous, microporous, perforated, or impermeable. The properties of the tape or sling may be selected based on the type of soft tissue anchor to which it will be coupled and the application for which the tape or sling will be used.

The implant 10 can also be one or more sutures. The suture(s) can be fabricated from one or more bio-compatible materials, including polypropylene, polyesters, polyolefins, polytetrafluoroethylene, polyethylene, polyurethanes, nylons, and co-polymers thereof.

The implant 10 may be coupled to the soft tissue anchor 1 by a number of methods, including tying, threading, crimping, affixing with an adhesive, or the like. The choice of the method of coupling to the proximal portion 8 is determined by the type of the implant 10 and the corresponding coupling structure of the soft tissue anchor 1. Alternatively, the soft tissue anchor 1 and the implant 10 can be fabricated as a single continuous unit.

Figure 22A:
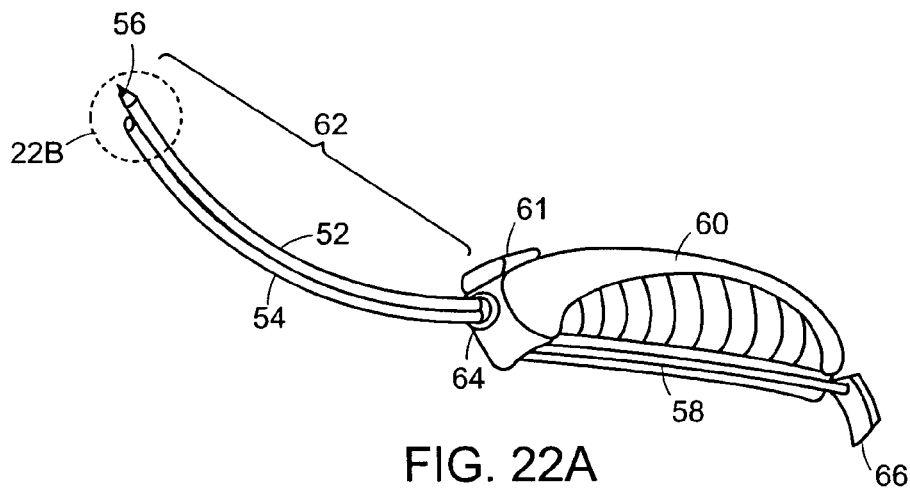
FIG. 22a is a side perspective view of an embodiment of a soft tissue anchor delivery device.

The soft tissue anchor 1 is positioned within the patient's body by way of a delivery device, such as the delivery device 50 of FIG. 22a. Referring to FIG. 22a, in one embodiment, the delivery device 50 includes a first cannula 52, a second cannula 54, a retractable trocar 56, a cartridge 58, and a handle 60. The retractable trocar 56 is operatively joined through the distal end of the handle 60 to a button 61.

Figure 22B:
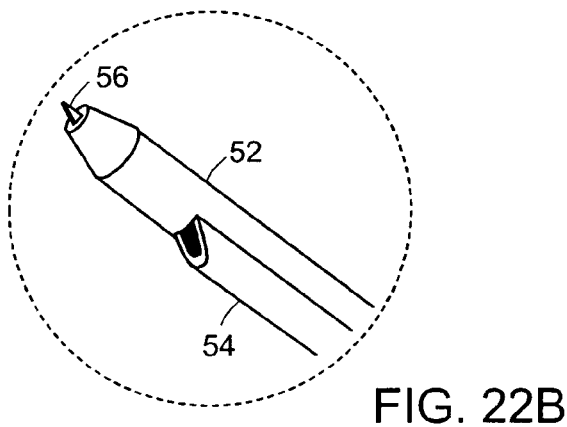

Referring again to FIG. 22a, the first cannula 52 and the second cannula 54 are cojoined lengthwise to form a probe 62, such that the lumen of the first cannula 52 and the lumen of the second cannula 54 are parallel. Referring to FIG. 22b, the distal end of the first cannula 52 can extend beyond the distal end of the second cannula 54 in the probe 62. The first cannula 52 and the second cannula 54 are rigid and can be made of materials such as stainless steel, plated carbon steel, or coated carbon steel. The proximal end of probe 62 is joined to the distal end of the handle 60 at an aperture 64 so that the first cannula 52 is on the same side of the handle 60 as the button 61.

The probe 62 forms an arc from the distal end of the probe 62 to about 10-75% of the length of the probe 62. For example, referring to FIG. 22a, the probe 62 forms an arc with the concave surface of the arc on the same side of the probe 62 as the button 61 of the handle 60. The arc of the probe 62 is selected to optimize the ease of insertion of the delivery system though the patient's tissues to position the implant 10 at the appropriate site within the patient's body.

The retractable trocar 56 is slidably positioned in the lumen of the first cannula 52. The point of the trocar 56 can be articulated from a retracted position to an extended position. The button 61 is operatively joined to the trocar 56. When the button 61 is depressed, the point of the trocar 56 is extended from the distal end of the first cannula 52. When the button 61 is released, the point of the trocar 56 is retracted into the first cannula 52. The button 61 is spring biased so that the operator must manually hold the button 61 down to extend the point of the trocar 56 from the distal end of the first cannula 52.

Figure 23A:
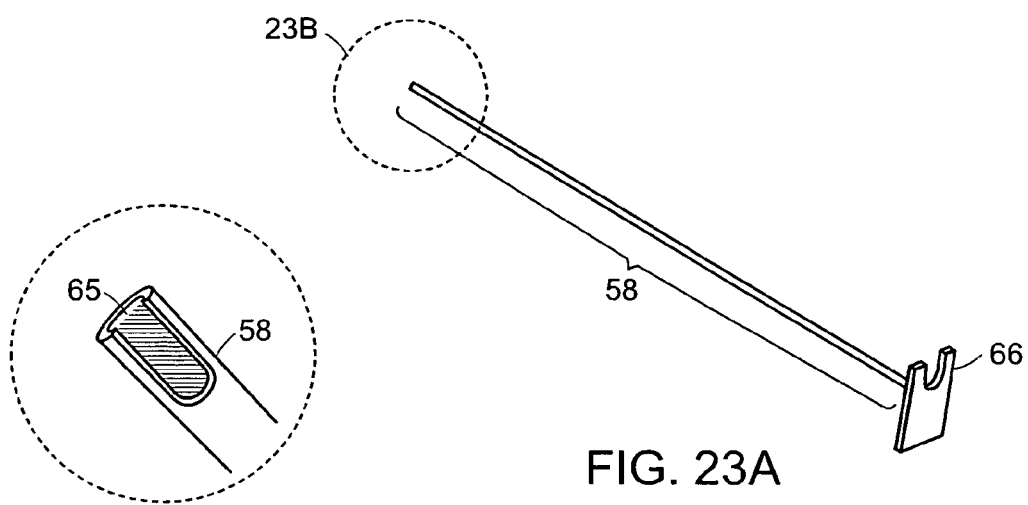
FIG. 23a is a view of an embodiment of a cartridge for use with the delivery device of FIG. 22a and/or FIG. 25.
Figure 23B:

Referring to FIG. 23a, the cartridge 58 is joined at its proximal end to a cartridge tab 66. Referring to FIG. 23b, the distal end of the cartridge 58 can include a structure (for example, a groove 65) for releasably engaging the soft tissue anchor 1. The cartridge 58 is made of a flexible material so it can follow the arc of the second cannula 54. The cartridge 58 can be completely removed from the handle 60 to load the soft tissue anchor 1 and the implant 10 into the second cannula 54. The cartridge 58 is then slidably positioned within the lumen of the second cannula 54. The soft tissue anchor 1 is moved toward the distal end of the second cannula 54 by moving the cartridge tab 66 forward toward the distal end of the handle 60.

Figure 24:
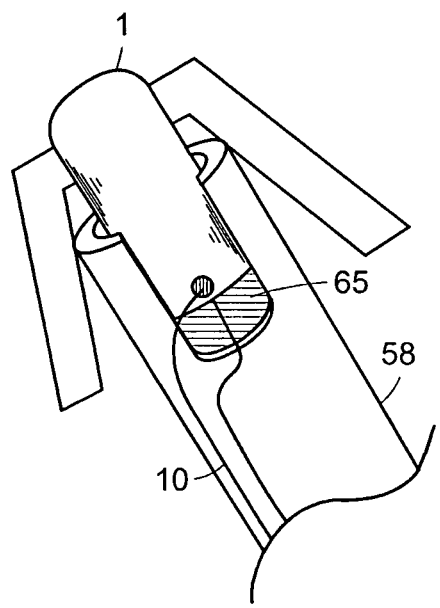
FIG. 24 is a view of a soft tissue anchor according to the invention releasably engaged by a groove in the distal end of the cartridge of FIG. 23b.

The first step in inserting the soft tissue anchor 1 into a patient's body is to load the soft tissue anchor 1 into the second cannula 54. The soft tissue anchor 1 can be inserted into the proximal end of the second cannula 54, followed by the cartridge 58. Alternatively, the soft tissue anchor 1 can first be engaged by a structure, such as a groove 65, included in the distal end of cartridge 58, as illustrated by FIG. 24. The cartridge 58 is then inserted into the second cannula 54. While inside the second cannula 54, each of the support members 4 of the soft tissue anchor 1 assumes the first position. The cartridge tab 66 is pushed toward the distal end of the handle 60 so that the soft tissue anchor 1 does not extend beyond the distal end of the second cannula 54.

The distal end of probe 62 is then inserted into a body cavity. As the probe 62 is advanced within the body cavity, the button 61 is depressed to extend the trocar 56 from the distal end of the first cannula 52 when it is necessary to penetrate and pass through soft tissue. Likewise, the button 61 is released to retract the trocar 56 into the first cannula 52 when no penetration is necessary. When the distal end of the probe 62 reaches the appropriate site within the body cavity, the cartridge tab 66 is moved as far distally as possible, which pushes the soft tissue anchor 1 out of the distal end of the second cannula 54. Once the soft tissue anchor 1 has left the distal end of the second cannula 54, each of the support members 4 assumes the second position, which inhibits the soft tissue anchor 1 from passing back through the soft tissue when a pull-back force is applied to the soft tissue anchor 1 by the implant 10. As soon as the soft tissue anchor 1 is in place, the probe 62 is removed from the body cavity, leaving the soft tissue anchor 1 and the implant 10 in place within the patient's body.

Figure 25:
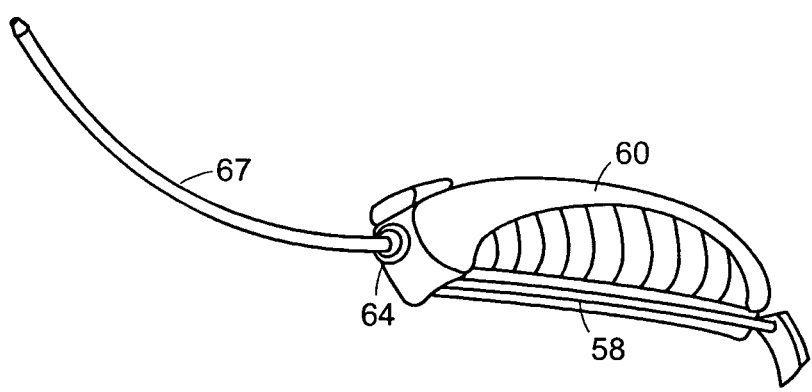
FIG. 25 is a side perspective view of another embodiment of a soft tissue anchor delivery device.

Referring to FIG. 25, in another embodiment, the delivery device 50 is suitable for delivering a soft tissue anchor 1 that has a distal portion 6 that tapers to a point 20, as illustrated, for example, by FIG. 10. The delivery device 50 includes a cannula 67, a cartridge 58, and a handle 60. The cannula 67 is rigid and can be made of a material such as stainless steel, plated carbon steel, or coated carbon steel. The proximal end of the cannula 67 is joined to the distal end of handle 60 at aperture 64.

The cannula 67 forms an arc from the distal end of the cannula 67 to about 10-75% of the length of the cannula 67. For example, referring to FIG. 25, the cannula 67 forms an arc with the concave surface of the arc on the same side of the cannula 67 as the top of the handle 60. The arc of the cannula 67 is selected to optimize the ease of insertion of the delivery system though the patient's tissues to position the implant 10 at the appropriate site within the patient's body.

Referring again to FIG. 23*a*, the cartridge 58 is joined at its proximal end to a cartridge tab 66. The distal end of the cartridge 58 can include a structure for releasably engaging the soft tissue anchor 1, for instance, a groove 65, as illustrated by FIG. 23*b*. The soft tissue anchor 1 can be inserted into the proximal end of the cannula 67 followed by the cartridge 58. Alternatively, the soft tissue anchor 1 can be first engaged by the distal end of the cartridge 58, as illustrated by FIG. 24, and then the cartridge 58 can be slid into the cannula 67. While inside the lumen of the cannula 67, each of the support members 4 of the soft tissue anchor 1 assumes the first position.

The cartridge 58 can move between three positions—positions A, B and C—by moving the cartridge tab 66 forward toward the distal end of the handle 50 and back toward the proximal end of the handle 50. Referring to FIGS. 26*a* and 26*b*, in position A, no portion of the soft tissue anchor 1 extends beyond the distal end of the cannula 67. Referring to FIGS. 27*a* and 27*b*, in position B, only the point 20 of the soft tissue anchor 1 is extended beyond the distal end of the cannula 67. Referring to FIG. 28, in position C, the soft tissue anchor 1 is pushed out of the distal end of the cannula 67.

The soft tissue anchor 1 is inserted into a patient's body by first loading the soft tissue anchor 1 into the cannula 67. As the cannula 67 is inserted into the body cavity, the cartridge tab 66 is moved to position B, where the point 20 extends from the distal end of the cannula 67, when it is necessary to penetrate and pass through soft tissue. The cartridge tab 66 is moved to position A, where the point 20 is retracted within the distal end of the cannula 67, when no penetration is necessary. When the distal end of the cannula 67 reaches the appropriate anatomical site, the cartridge tab 66 is moved to position C, which pushes the soft tissue anchor 1 out of the distal end of the cannula 67. Once the soft tissue anchor 1 has left the distal end of the cannula 67, each of the support members 4 assumes the second position, which inhibits the soft tissue anchor 1 from passing back through the soft tissue when a pull-back force is applied to the soft tissue anchor 1 by the implant 10. As soon as the soft tissue anchor 1 is in place, the cannula 67 is removed from the body cavity, leaving the soft tissue anchor 1 and the implant 10 in place within the patient's body.

Figure 29:
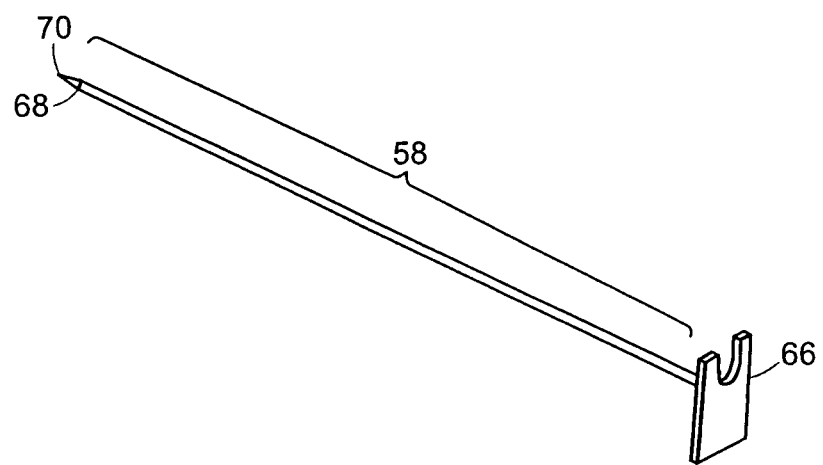
FIG. 29 is a view of another embodiment of a cartridge, with a distal portion that tapers to a point.
Figure 30:
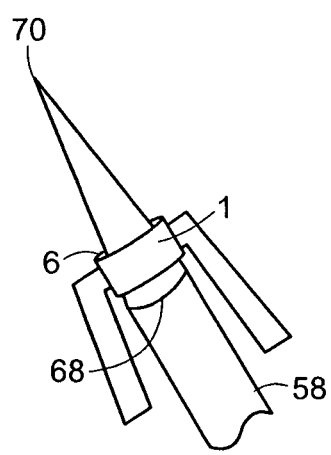
FIG. 30 is a view of the pointed distal end of the cartridge of FIG. 29, with the soft tissue anchor of FIGS. 11a and 11b disposed thereon.

In another embodiment, the delivery device 50 illustrated by FIG. 25 is used to deliver a soft tissue anchor 1 that has a hollow central body element 2, as illustrated, for example, by FIGS. 11*a* and 11*b*. In this embodiment, the distal end of the cartridge 58 tapers from an edge 68 to a point 70, as illustrated by FIG. 29. Referring to FIG. 30, when the cartridge 58 is threaded through the aperture 22 in the soft tissue anchor 1, the point 70 extends beyond the distal end 6 of the soft tissue anchor 1, and the soft tissue anchor 1 can move no farther down the length of the cartridge 58 than the edge 68.

Referring again to FIG. 25, the cartridge 58 is slid into the lumen of the cannula 67 of the delivery device 50. While inside the lumen of the cannula 67, each of the support members 4 of the soft tissue anchor 1 assumes the first position. The cartridge 58 can move between three positions—positions A, B and C—by moving the cartridge tab 66 forward toward the distal end of the handle 50 and back toward the proximal end of the handle 50. Referring to FIGS. 31*a* and 31*b*, in position A, the point 70 of the cartridge 58 is fully retracted within the distal end of the cannula 67. Referring to FIGS. 32*a* and 32*b*, in position B, only the point 70 of the cartridge 58 is extended beyond the distal end of the cannula 67. Referring to FIG. 33, in position C, the soft tissue anchor 1 is pushed out of the distal end of the cannula 67.

The soft tissue anchor 1 is inserted into a patient's body by first threading the distal end of the cartridge 58 through the aperture in the soft tissue anchor 1. Cartridge 58 is inserted into the cannula 67. As the cannula 67 is inserted into the body cavity, the cartridge tab 66 is moved to position B, where the point 70 extends from the distal end of the cannula 67, when it is necessary to penetrate and pass through soft tissue. The cartridge tab 66 is moved to position A, where the point 70 is retracted within the distal end of the cannula 67, when no penetration is necessary. When the distal end of the cannula 67 reaches the appropriate site within the body cavity, the cartridge tab 66 is moved to position C, which pushes the soft tissue anchor 1 out of the distal end of the cannula 67. Once the soft tissue anchor 1 has left the distal end of the cannula 67, each of the support members 4 assumes the second position, which inhibits the soft tissue anchor 1 from passing back through the soft tissue when a pull-back force is applied to the soft tissue anchor 1 by the implant 10. As soon as the soft tissue anchor 1 is in place, the cannula 67 is removed from the body cavity, leaving the soft tissue anchor 1 and the implant 10 in place within the patient's body.

The foregoing descriptions of delivery devices and systems for positioning a soft tissue anchor within a patient's body illustrative and not restrictive. A suitable delivery device or system can be embodied in other specific forms.

The present invention can find use in a number of female pelvic floor reconstruction procedures, including the correction of vaginal, uterine, and rectal prolapses, repair of cystoceles, lateral defect repair, and for the treatment of urinary incontinence. The present invention also can be useful in procedures dealing with male patients. In one embodiment, the soft tissue anchor 1 is used to support a surgical mesh used for the treatment of female stress urinary incontinence (SUI).

Figure 34:
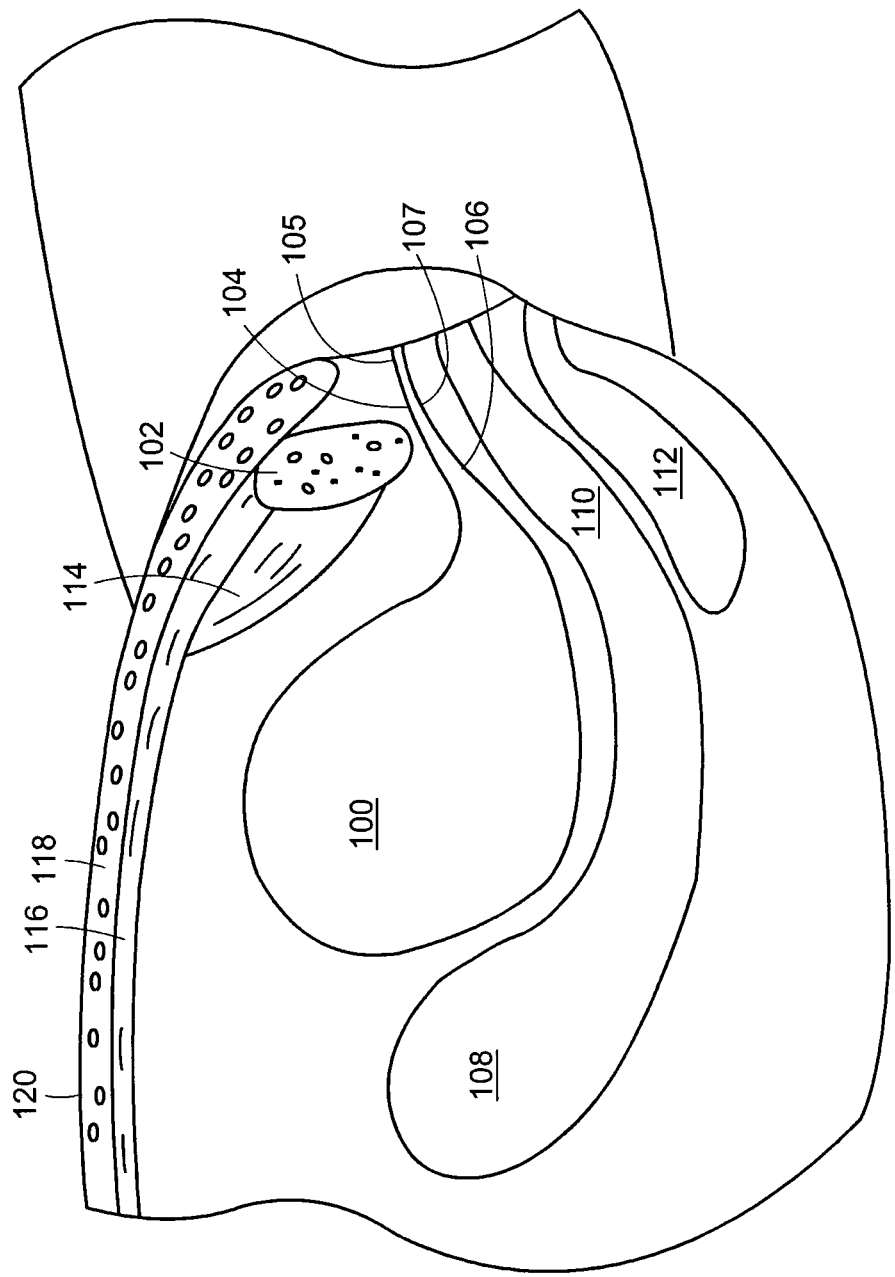
FIG. 34 is a cross section of a female patient's pelvic region.

FIG. 34 illustrates a simplified cross-sectional view of a female patient's pelvic region. The bladder 100 is located behind the pubic bone 102. The urethra 104 extends from the bladder 100 toward the urinary meatus 105. The upper portion of the urethra 104 constitutes the urethrovesical junction 106, or the bladder neck. Support of the middle portion 107 of the urethra 104, between the urethrovesical junction 106 and the urinary meatus 105, is believed to be important for the treatment of SUI. The uterus 108, located behind the bladder 100, leads to the vagina 110. The rectum 112 is located behind the vagina. The rectus abdominus muscle 116, which is attached to the pubic bone 102 by Cooper's ligament 114, is located above the bladder 100 and the uterus 104. A subcutaneous fat layer 118 is located between the rectus abdominus 116 and the skin 120.

The maintenance of normal female continence depends upon the proper support and stabilization of the bladder 100 and the urethra 104, especially during period of abdominal stress, such as when the patient coughs or laughs. SUI can be caused by the weakening or stretching of the ligaments or other tissues that support the urethra 104 to the point where the urethra 104 cannot prevent the release of urine during periods of abdominal stress. The present invention can be used to treat SUI by providing the urethral support necessary to maintain urinary continence.

Figure 35:
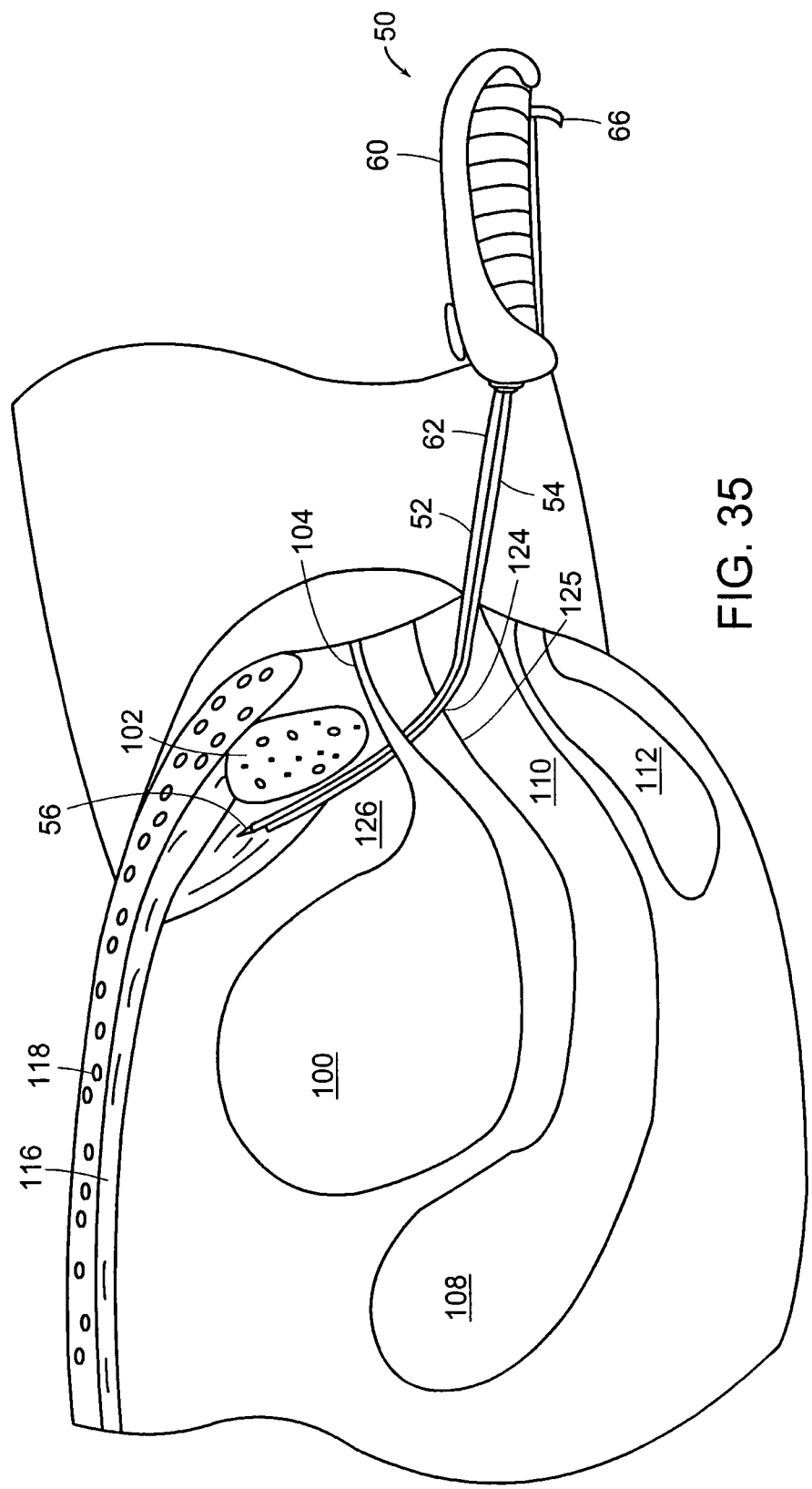
FIG. 35 is a cross section corresponding to FIG. 34, showing a delivery device according to the invention just prior to passage through the rectus abdominus.

Referring to FIG. 35, a soft tissue anchor 1, to which a surgical mesh 122 has been coupled, is loaded into a delivery device 50, which includes a first cannula 52 and a second cannula 54 that are cojoined lengthwise to form a probe 62. An incision 124 is made in the vaginal wall 125 directly beneath the urethra 104. The distal end of the probe 62 is inserted into the incision 124, and the probe is guided along one side of the urethra 104. The retractable trocar 56 is extended from the distal end of the first cannula 52 in order to pierce the endopelvic tissue 126 and move the probe upward toward the rectus abdominus 116.

Figure 36:
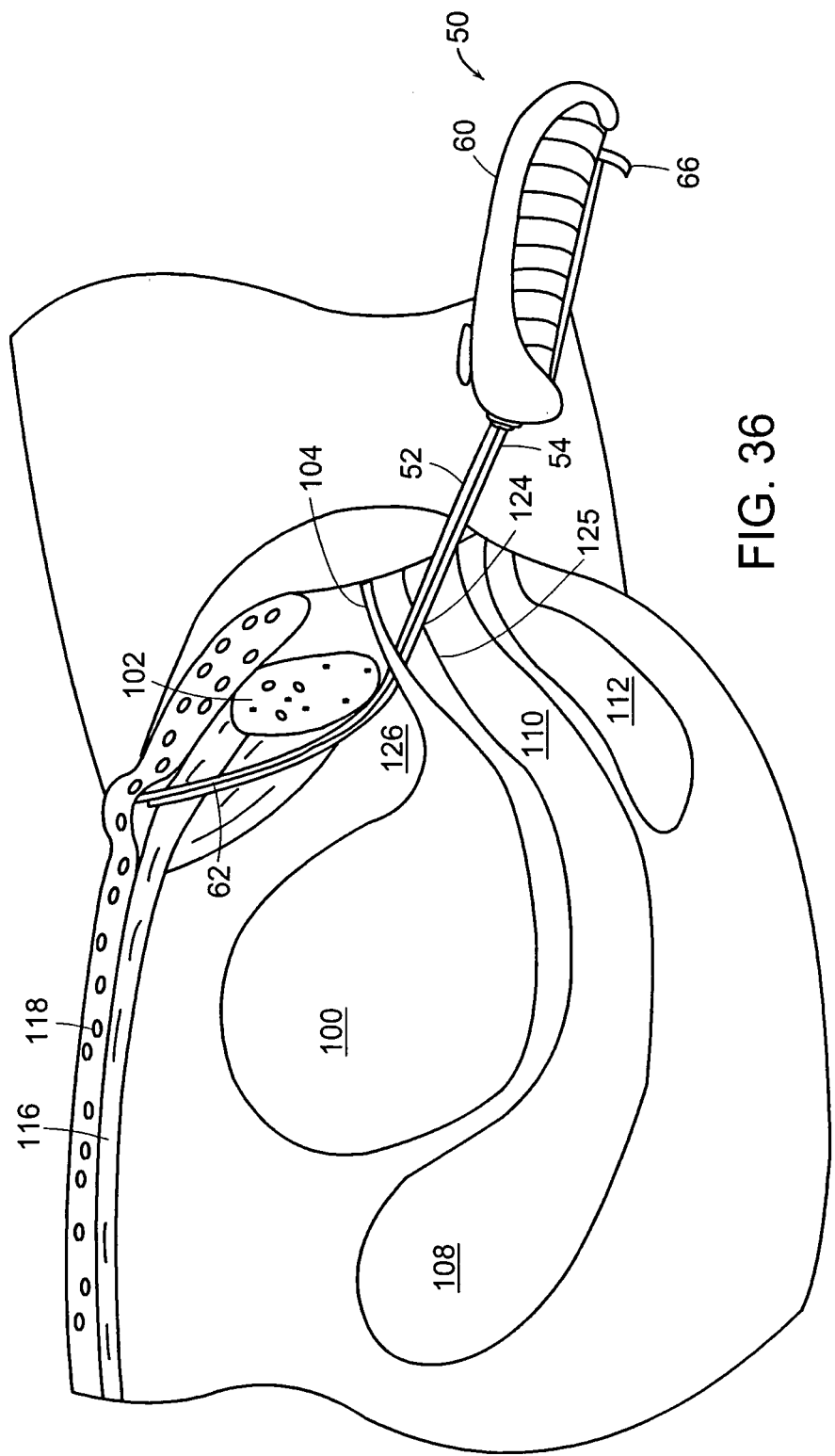
FIG. 36 is a cross section corresponding to FIG. 34, showing a delivery device according to the invention just after passage through the rectus abdominus.

Referring to FIG. 36, once the distal end of the probe 62 pierces the rectus abdominus 116, the trocar 56 is retracted into the first cannula 52, and the probe 62 is advanced further, pushing the subcutaneous fat layer 118 upward and separating it from the rectus abdominus 116, but not penetrating it. The soft tissue anchor 1 is ejected from the distal end of the second cannula 54 by advancing the cartridge tab 66 toward the distal end of the handle 60. Once the soft tissue anchor 1 is deployed, the probe 62 is pulled back out of the incision, leaving the soft tissue anchor 1 resting on the rectus abdominus 116 beneath the subcutaneous fat layer 118.

Figure 37:
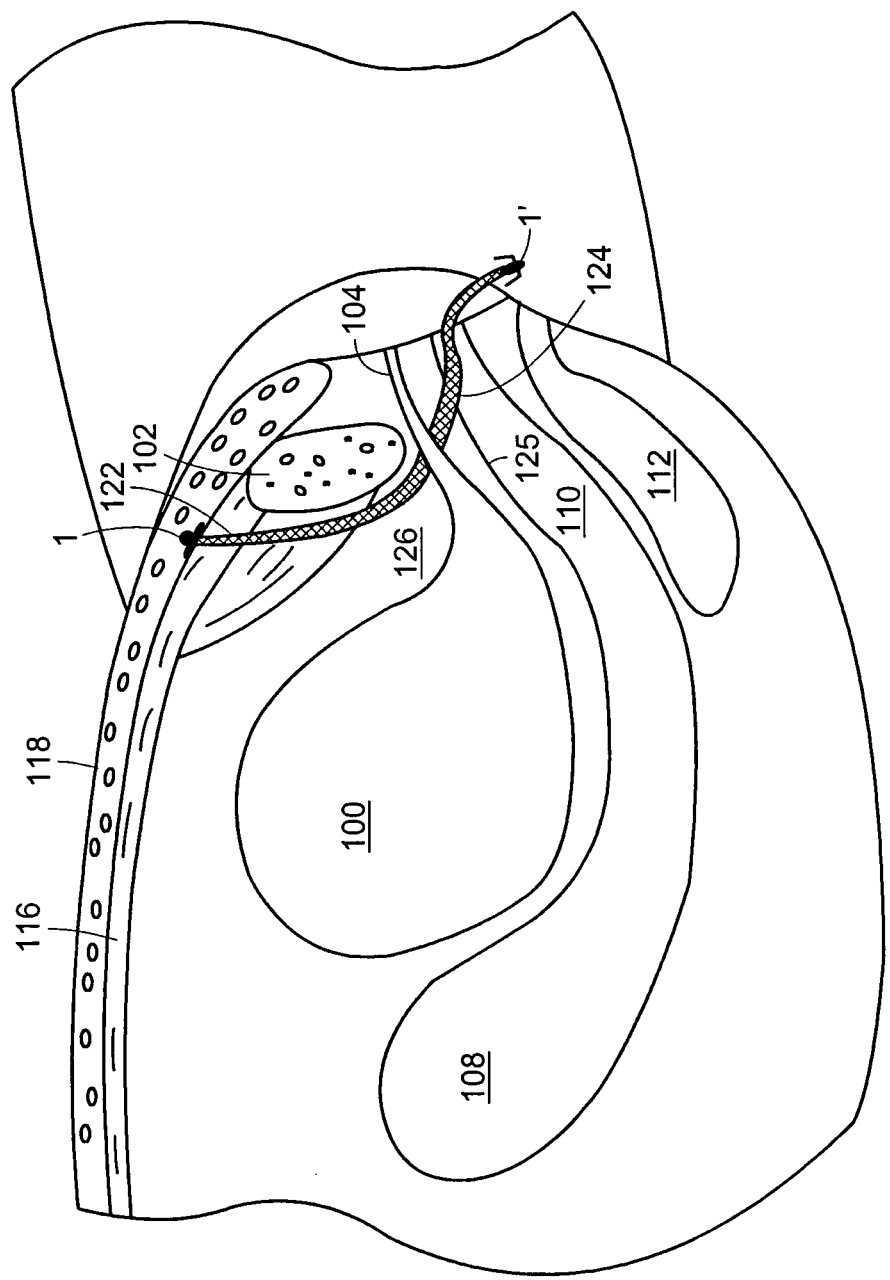
FIG. 37 is a cross section corresponding to FIG. 34, showing a soft tissue anchor according to the invention in place between the rectus abdominus and the subcutaneous fat layer and an implant leading from the soft tissue anchor, through the endopelvic fascia, and out through the vagina.
Figure 38:
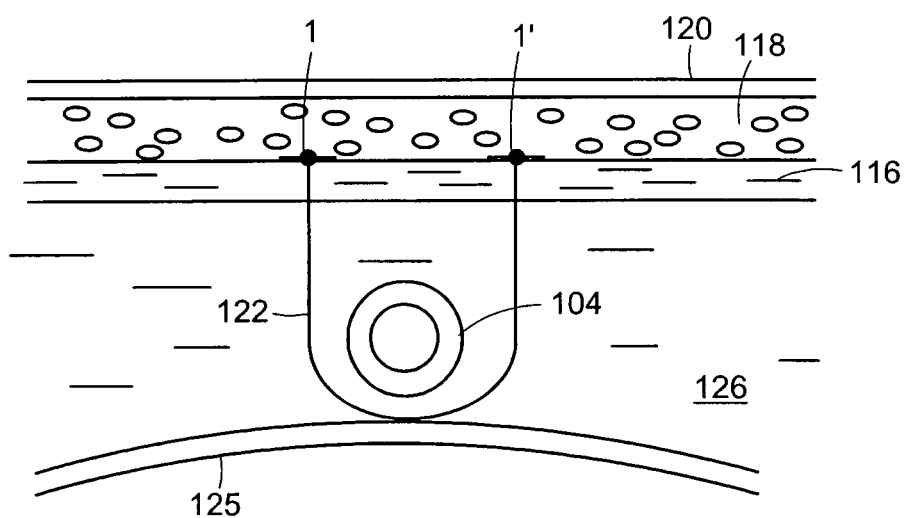
FIG. 38 is a sectional view of a female patient's pelvic region, showing an implant supported by two soft tissue anchors according to the invention.

As the probe 62 is removed, the surgical mesh 122, which is coupled to the embedded soft tissue anchor 1, is pulled out of the distal end of the second cannula 54. Referring to FIG. 37, the surgical mesh 122 trails from the soft tissue anchor 1, through the endopelvic tissue 126 along one side of the urethra 104, and into the vagina 110 through the incision 124 in the vaginal wall 125. The end of the surgical mesh 122 which is trailing in the vagina typically is already coupled to a second soft tissue anchor 1', which is then loaded into the delivery device 50. The above procedure is repeated advancing the probe 62 along the other side of the urethra 104 and implanting the second soft tissue anchor 1' between subcutaneous fat layer 118 and the rectus abdominus 116. Referring to FIG. 38, the surgical mesh 122, held in position by the two tissue anchors 1 and 1', provides the urethral support necessary for the treatment of SUI.

Although the above description refers to a surgical mesh, a number of different implant structures and materials could be employed with the current invention, including one or more sutures or a surgical sling, for example.

Figure 39:
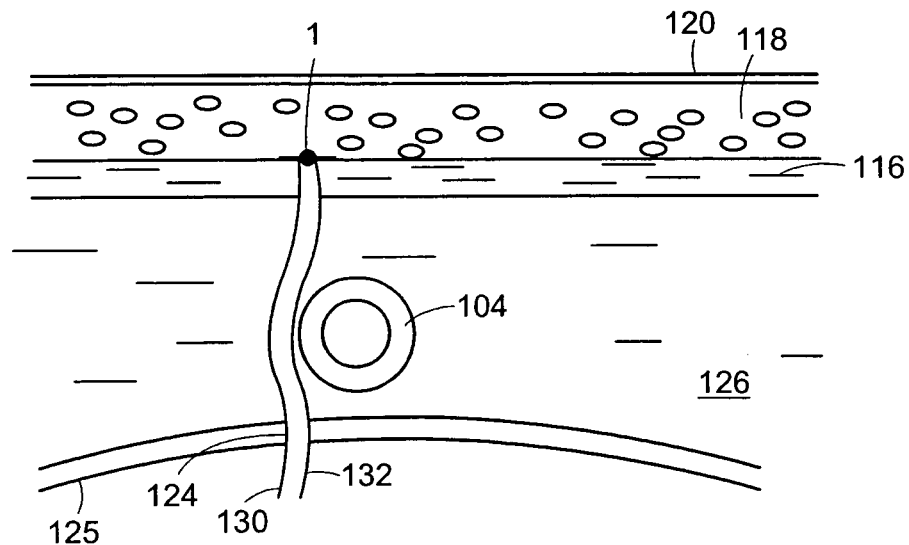
FIG. 39 is a sectional view corresponding to FIG. 38, showing a soft tissue anchor according to the invention in place between the rectus abdominus and the subcutaneous fat layer and two sutures leading from the soft tissue anchor, through the endopelvic fascia, and out through the vagina.
Figure 40:
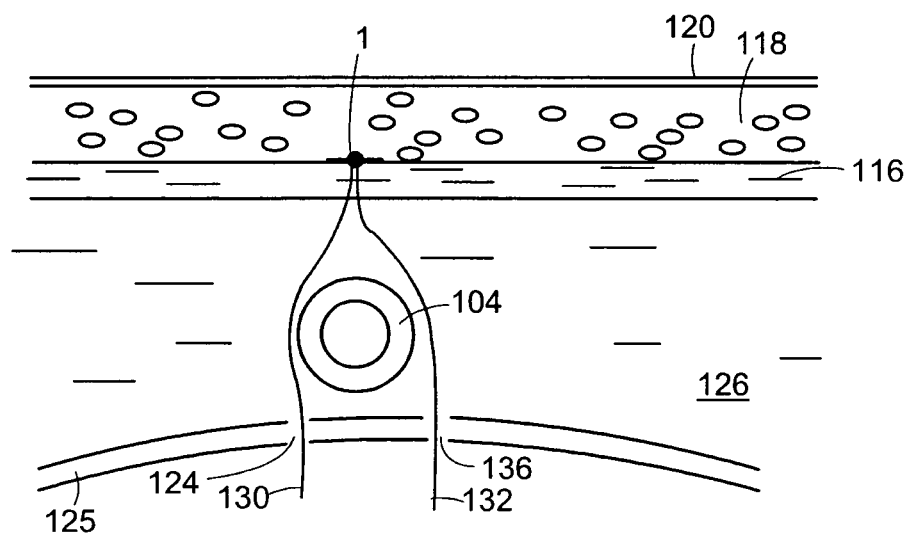
FIG. 40 is a sectional view corresponding to FIG. 39, showing the two sutures after one has been moved to the opposite side of the urethra.
Figure 41:
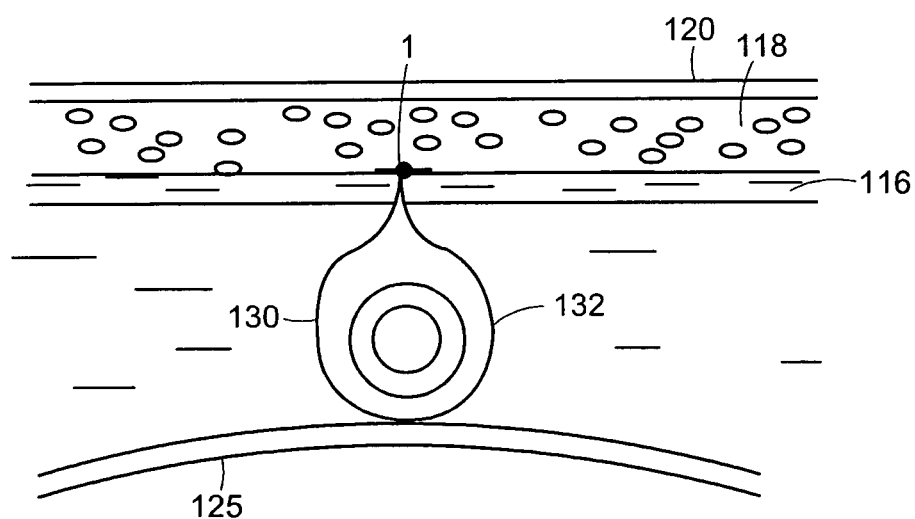
FIG. 41 is a sectional view corresponding to FIG. 39, showing the two sutures joined beneath the urethra and forming a loop around the urethra.

Alternatively, a single soft tissue anchor 1 can be used to anchor an implant to soft tissue for use in pelvic floor reconstruction procedures, such as the treatment of SUI. For example, referring to FIG. 39, a soft tissue anchor 1 that is coupled to two sutures, 130 and 132, can be implanted between subcutaneous fat layer 118 and the rectus abdominus 116 as described above. One of the sutures can then be passed back through the incision 124 in the vaginal wall 125, over the urethra 104, and through a second incision 136 in the vaginal wall 125, as illustrated by FIG. 40. The ends of the two sutures 130 and 132 can then be joined together beneath the urethra 104, forming a loop around the urethra 104, as illustrated by FIG. 41. The ends of the two sutures can also be joined to another implant, such as a surgical mesh or surgical sling, placed beneath the urethra.

The implant used for pelvic floor reconstruction procedures can be pre-coupled to one or more soft tissue anchors according to the invention, and this implant/anchor unit can be sold separately or together with a suitable delivery system. Surgeons and/or other medical professionals can then use the implant/anchor unit to perform surgical procedures, for example, pelvic floor reconstruction procedures.

The invention may be embodied in other specific forms without departing from the spirit or essential characteristics thereof. The disclosed embodiments are to be considered in all respects illustrative and not restrictive. The scope of the invention is not limited just to the disclosed embodiments.

What is claimed is:

1. A sling assembly, comprising:
   a sling, and
   a soft tissue anchor comprising a central body element having a proximal sling engaging portion for receiving the sling and at least one radially extending arm disposed about the central body element, the at least one arm having first and second ends, a compliant middle portion, a first rigid portion between the first end and the compliant middle portion, and a second rigid portion between the compliant middle portion and the second end, the first end being pivotable about the distal end of the central body element and the second end unattached to the central body element and proximal of the first end.

2. The sling assembly of claim 1, wherein the at least one arm has a first position proximate to the central body element and a second position pivoted outward from the central body element.

3. The sling assembly of claim 2, wherein the at least one arm is biased in the second position.

4. The sling assembly of claim 1, wherein the compliant middle portion allows the second portion to move closer to the first portion to form a collapsed position of the at least one arm in which an angle between the first and second portions is less than 90 degrees.

5. The sling assembly of claim 1, wherein the central body element defines an aperture and a passageway through its center.

6. The sling assembly of claim 1, wherein the sling engaging portion of the soft tissue anchor is one of an aperture, an eyelet, a lumen, and a groove.

7. The sling assembly of claim 1, wherein at least some of the proximal portion of the soft tissue anchor includes threads.

8. The sling assembly of claim 1, wherein the sling is one of a mesh sling, and a tape.

9. The sling assembly of claim 1, wherein the soft tissue anchor is made of at least one bio-compatible material.

10. The sling assembly of claim 9, wherein the at least one bio-compatible material is one of a metal and a polymer.

11. The sling assembly of claim 2, wherein the first position permits passage of the anchor through soft tissue, and the second position inhibits passage of the soft tissue anchor back through the soft tissue.

12. The sling assembly of claim 1, wherein the at least one arm is a plurality of arms.

13. The sling assembly of claim 4, wherein the at least one arm is biased to be in the collapsed position.

* * * * *